(12) United States Patent
Shimada et al.

(10) Patent No.: US 8,372,053 B2
(45) Date of Patent: Feb. 12, 2013

(54) PANTS-TYPE DISPOSABLE WEARING ARTICLE

(75) Inventors: Takaaki Shimada, Kagawa-ken (JP);
Takako Uosawa, Kagawa-ken (JP);
Naoko Takada, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 782 days.

(21) Appl. No.: 10/764,589

(22) Filed: Jan. 27, 2004

(65) Prior Publication Data

US 2004/0186453 A1    Sep. 23, 2004

(30) Foreign Application Priority Data

Jan. 30, 2003   (JP) .................................. 2003-22646

(51) Int. Cl.
*A61F 13/15* (2006.01)
(52) U.S. Cl. ................................................. 604/385.27
(58) Field of Classification Search ............... 604/385.2, 604/358, 378, 385.24–385.29
See application file for complete search history.

(56) References Cited

U.S. PATENT DOCUMENTS

| | | | |
|---|---|---|---|
| 5,171,239 A | 12/1992 | Igaue et al. | |
| 5,415,649 A * | 5/1995 | Watanabe et al. | 604/385.29 |
| 5,575,783 A | 11/1996 | Clear et al. | |
| 5,745,922 A | 5/1998 | Rajala et al. | |
| 5,817,087 A | 10/1998 | Takabayashi et al. | |
| 5,846,232 A | 12/1998 | Serbiak et al. | |
| 6,045,543 A * | 4/2000 | Pozniak et al. | 604/385.01 |
| 6,049,916 A | 4/2000 | Rajala et al. | |
| 6,297,424 B1 | 10/2001 | Olson et al. | |
| 6,595,976 B2 | 7/2003 | Jitoe et al. | |
| 6,923,797 B2 * | 8/2005 | Shinohara et al. | 604/385.27 |
| 2002/0049421 A1 | 4/2002 | Hayase et al. | |
| 2004/0006323 A1 * | 1/2004 | Hall et al. | 604/385.24 |

FOREIGN PATENT DOCUMENTS

| | | |
|---|---|---|
| EP | 0761193 | 8/1996 |
| EP | 0761194 | 8/1996 |
| EP | 0762293 | 8/1996 |
| EP | 0 761 193 | 3/1997 |
| EP | 0990434 | 10/1999 |
| EP | 0990434 | 4/2000 |
| EP | 1157681 | 11/2001 |
| EP | 761193 B1 * | 12/2001 |
| EP | 761194 B1 * | 12/2001 |
| EP | 1184012 | 3/2002 |

(Continued)

OTHER PUBLICATIONS

EP 0761194 A2, Disposable Under Garment, Filing Date: Aug. 22, 1996, Uni-charm Corporation, Inventor: Yamamoto, Masamito et al.*

(Continued)

*Primary Examiner* — Melanie Hand
(74) *Attorney, Agent, or Firm* — Lowe Hauptman Ham & Berner LLP

(57) ABSTRACT

A pants-type disposable wearing article includes a liquid-impervious base sheet, a liquid-absorbent panel and transverse elastic members, each having opposite fixed portions secured to the lateral zones of the edges article, and a free portion extending in the transverse direction of the article between the opposite fixed portions across the panel and secured neither to the base sheet nor to the panel. The article further has leg-surrounding elastic members. At the crossover points of the transverse elastic members and the leg-surrounding elastic members, the elastic members are not secured one to another.

8 Claims, 15 Drawing Sheets

FOREIGN PATENT DOCUMENTS

| | | |
|---|---|---|
| EP | 1197195 | 4/2002 |
| JP | 08-084747 | 4/1996 |
| JP | 1997-38134 | 2/1997 |
| JP | 09-056747 | 3/1997 |
| JP | 09-099006 | 4/1997 |
| JP | 11-299829 | 11/1999 |
| JP | 2000-107225 | 4/2000 |
| JP | 2001-145666 | 5/2001 |
| JP | 2001-157690 | 6/2001 |
| JP | 2001157690 A * | 6/2001 |
| JP | 2001-231078 | 8/2001 |
| JP | 2002-095692 | 4/2002 |
| JP | 2003-038556 | 2/2003 |

OTHER PUBLICATIONS

EP 0762293 A2, Absorbent article of pants type, Filing Date: Aug. 1, 1996, Uni-charm Corporation, Inventor: Yamamoto, Masamito et al.*

English translation of JP 2001-157690 A.*

Patent Abstract of Japan; Publication No. 2002-095692 published Apr. 2, 2002 w/Japanese Application No. 2000-290745 filed Sep. 25, 2000.

Patent Abstract of Japan; Publication No. 2001-145666 published May 29, 2001 w/Japanese Application No. 11-329189 filed Nov. 19, 1999.

Patent Abstract of Japan; Publication No. 08-084747 published Apr. 2, 2002 w/Japanese Application No. 06-246732 filed Sep. 16, 2004.

Patent Abstract of Japan; Publication No. 08-084747 published Apr. 2, 2002 w/Japanese Application No. 07-221976 filed Aug. 30, 1995.

Patent Abstract of Japan; Publication No. 09-056747 published Mar. 4, 1997 with Japanese Application No. 07-221976 filed Aug. 30, 1995.

Patent Abstract of Japan; Publication No. 2001-157690 published Jun. 12, 2001 with Japanese Application No. 11-343511 filed Dec. 2, 1999.

European Search Report for Application No. 04704758.4 mailed Sep. 1, 2011.

* cited by examiner

PANTS-TYPE DISPOSABLE WEARING ARTICLE

BACKGROUND OF THE INVENTION

The present invention relates to a pants-type disposable wearing articles for absorption and containment of bodily discharges. The present application is based on, and claims priority from, Japanese Application Serial Number 2003-22646, filed Jan. 30, 2003, the disclosure of which is hereby incorporated by reference herein in its entirety.

There are well known in Japanese Patent Application Publication No. 1997-38134A, a pants-type disposable wearing articles comprising a liquid-pervious topsheet facing the wearer's skin, a liquid-impervious backsheet facing away the wearer's skin and a liquid-absorbent core interposed between these top- and backsheets, and configured to define front and rear waist regions opposed to each other, a crotch region extending between these waist regions, a waist-hole and a pair of leg-holes below the waist-hole wherein a plurality of waist-surrounding first elastic members, a plurality of waist-surrounding second elastic members and a plurality of leg-surrounding elastic members are contractibly attached to article.

The article disclosed in the above-cited Publication has a waist surrounding upper end zone extending in a transverse direction across the front and rear waist regions, lateral zones of the waist regions extending in a longitudinal direction and lateral zones of the crotch region extending in a leg-surrounding direction. In this article, the lateral zones of the waist regions are put flat and joined together in the vicinity of respective edges of the lateral zones of the waist regions by means of plural welding lines arranged intermittently in the longitudinal direction.

The waist-surrounding first elastic members are arranged to be spaced apart one from another by a given dimension in the longitudinal direction and to extend along the waist-surrounding upper end zone in the transverse direction. The waist-surrounding second elastic members are arranged below the first elastic members also to be spaced apart one from another by a given dimension in the longitudinal direction and to extend across the front and rear waist regions in the transverse direction. The leg-surrounding elastic members are arranged to be spaced apart one from another by a given dimension in the transverse direction and to extending along the lateral zones of the crotch region in the leg-surrounding direction. The first elastic members and the leg-surrounding elastic members are interposed between the top- and backsheets and joined to these sheets by means of hot melt adhesives. The portions of the second elastic members extending across the lateral zones of the waist regions are interposed between the top- and backsheets and joined with hot melt adhesive to these sheets. The portions of the second elastic members extending across the core in the transverse direction are interposed between the backsheet and the core and bonded to them by means of hot melt adhesives. In the areas of the lateral zones of the waist regions placed aside toward the crotch region, the second elastic members and the leg-surrounding elastic members three-dimensionally cross one another. The above-cited Publication describes the effect such that the first elastic members cooperate with the second elastic members to tighten the article around the wearer's waist region and thereby to reliably prevent the article from slipping down along the wearer's waist region.

With the article disclosed in the above-cited Publication, assumed that the waist-surrounding second elastic members and the leg-surrounding elastic members are secured together at crossover points of these elastic members, there is an anxiety that a contractile force of the leg-surrounding elastic members might pull the second elastic members in the leg-surrounding direction to hinder a desired contraction of the second elastic members in the transverse direction, on one hand, and a contractile force of the second elastic members might pull the leg-surrounding elastic members in the transverse direction to hinder a desired contraction of the leg-surrounding elastic members, on the other hand. If the desired contraction of the waist-surrounding second elastic members and/or the leg-surrounding elastic members is hindered by the contraction of the leg-surrounding elastic members and/or the waist-surrounding elastic members, respectively, the waist-surrounding second elastic members can not tighten the article around the wearer's waist and/or the leg-surrounding elastic members can not tighten the article around the wearer's legs. Such situation may cause the article to slip down along the wearer's waist and/or may cause bodily discharges from leaking sideways beyond the crotch's lateral zones. In addition, with this article disclosed in the above-cited Publication, the contractile force of the second elastic members in the transverse direction may act directly upon the core and may form a plurality of irregular wrinkles which deteriorate a liquid-absorbing function of the core. This is for the reason that the portions of the second elastic members extending across the core are joined to the core.

SUMMARY OF THE INVENTION

It is an object of the present invention to provide a pants-type disposable wearing article improved so that slip down of the article along the wearer's waist and sideway leakage of bodily discharges beyond the lateral zones of the crotch region can be effectively prevented by eliminating apprehension that the contractile force of the waist-surrounding second elastic members and/or the leg-surrounding elastic members might hinder the desired contraction of the leg-surrounding elastic members and/or the waist-surrounding second elastic members, respectively. It is an additional object of the present invention to provide a pants-type disposable wearing article improved so that a desired liquid absorbing function of the core can be maintained by sufficiently alleviating an effect of the contractile force of the second elastic members acting on the core to prevent the core from being formed with a plurality of irregular wrinkles.

The present invention is directed to a pants-type disposable wearing article. The article comprises a liquid-impervious base sheet defining front and rear waist regions opposed to each other and a crotch region extending between these waist regions and a liquid-absorbent panel extending over the crotch region and further into the front and rear waist regions, the base sheet having, in said front and rear waist regions, a waist-surrounding end zone extending in a transverse direction, a pair of waist lateral zones extending in a longitudinal direction and, in the crotch region, a pair of crotch lateral zones extending in a leg-surrounding direction. The base sheet is provided with a waist-surrounding first elastic member extending in the transverse direction along the waist-surrounding end zone so as to be contractible in the transverse direction, a plurality of waist-surrounding second elastic members lying below the first elastic members so as to be contractible in the transverse direction and a plurality of leg-surrounding elastic members extending along the crotch lateral zones in a leg-surrounding direction so as to be contractible in the leg-surrounding direction, the second elastic members being spaced apart one from another by a predetermined dimension from at least one of the front and rear waist regions toward the crotch region in the longitudinal direction, and the waist lateral zones being connected together to form a waist-hole and a pair of leg-holes.

The article further comprises the second elastic members having fixed portions secured to the waist lateral zones and the crotch lateral zones in vicinities of respective side edges of these lateral zones and free portions extending between the fixed portions across the panel in the transverse direction and secured neither to the base sheet nor to the panel; and the free portions of the second elastic members and the leg-surrounding elastic members three-dimensionally intersecting one another in the crotch lateral zones and ranges of the waist lateral zones placed aside toward the crotch region, at least the crotch lateral zones and not secured together at crossover points of these elastic members.

The present invention includes the following preferred embodiments.

The fixed portions of the second elastic members extending in the crotch region are placed aside toward the side edges of the crotch lateral zones compared to the leg-surrounding elastic members.

The second elastic members extending in the waist lateral zones contract to a transverse dimension which is substantially the same as or slightly larger than a transverse dimension of the panel as measured between transversely opposite side edges.

The base sheet comprises a first sheet lying on the side of the panel and a second sheet lying outside the first sheet; and the first and second elastic members as well as the leg-surrounding elastic members are interposed between the first sheet and the second sheet.

The base sheet has a third sheet interposed between the first sheet and the second sheet; the second elastic members are interposed between the first and third sheets or between the second and third sheets; the leg-surrounding elastic members are interposed between the pair of sheets other than the pair of sheets sandwiching the second elastic members; and the second elastic members and the leg-surrounding elastic members are spaced apart one from another with the third sheet lying therebetween.

A plurality of welded spots at which the sheets sandwiching the second elastic members are formed in vicinities of the side edges of the panel so that the welded spots lie between each pair of the adjacent free portions of the second elastic members and are spaced one from another by a predetermined dimension in the longitudinal direction.

The panel comprises a liquid-pervious upper layer sheet facing a wearer's skin, a liquid-impervious lower layer sheet facing away from the wearer's skin and a liquid-absorbent core interposed between the upper and lower layer sheets, at least the upper layer sheet and the core.

DETAILED DESCRIPTION OF THE PREFERRED EMBODIMENTS

Details of a pants-type disposable wearing article according to the present invention will be more fully understood from the description given hereunder with to the accompanying drawings.

Figure 1:
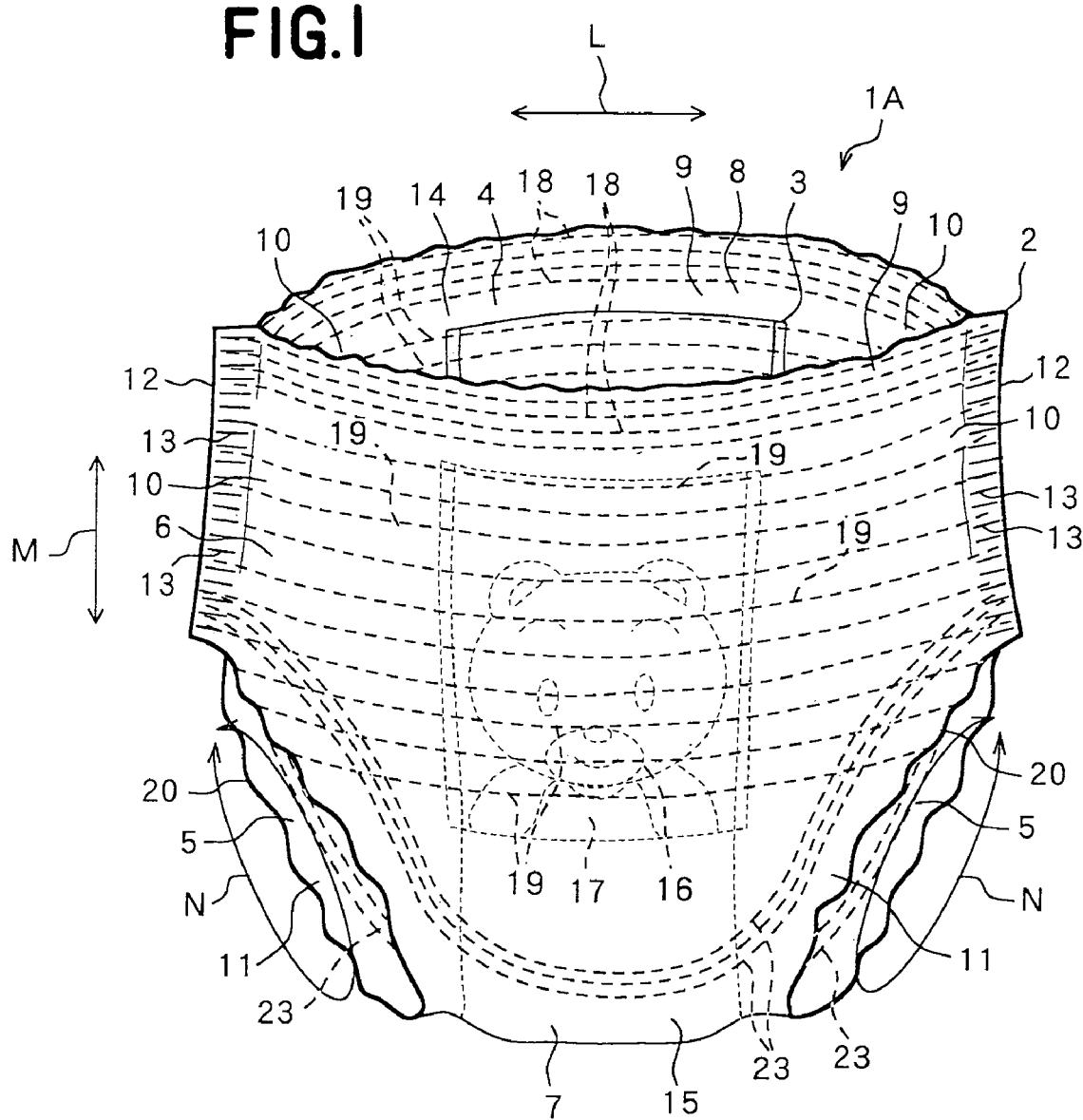
FIG. 1 is a perspective view showing an example of the wearing article.
Figure 2:
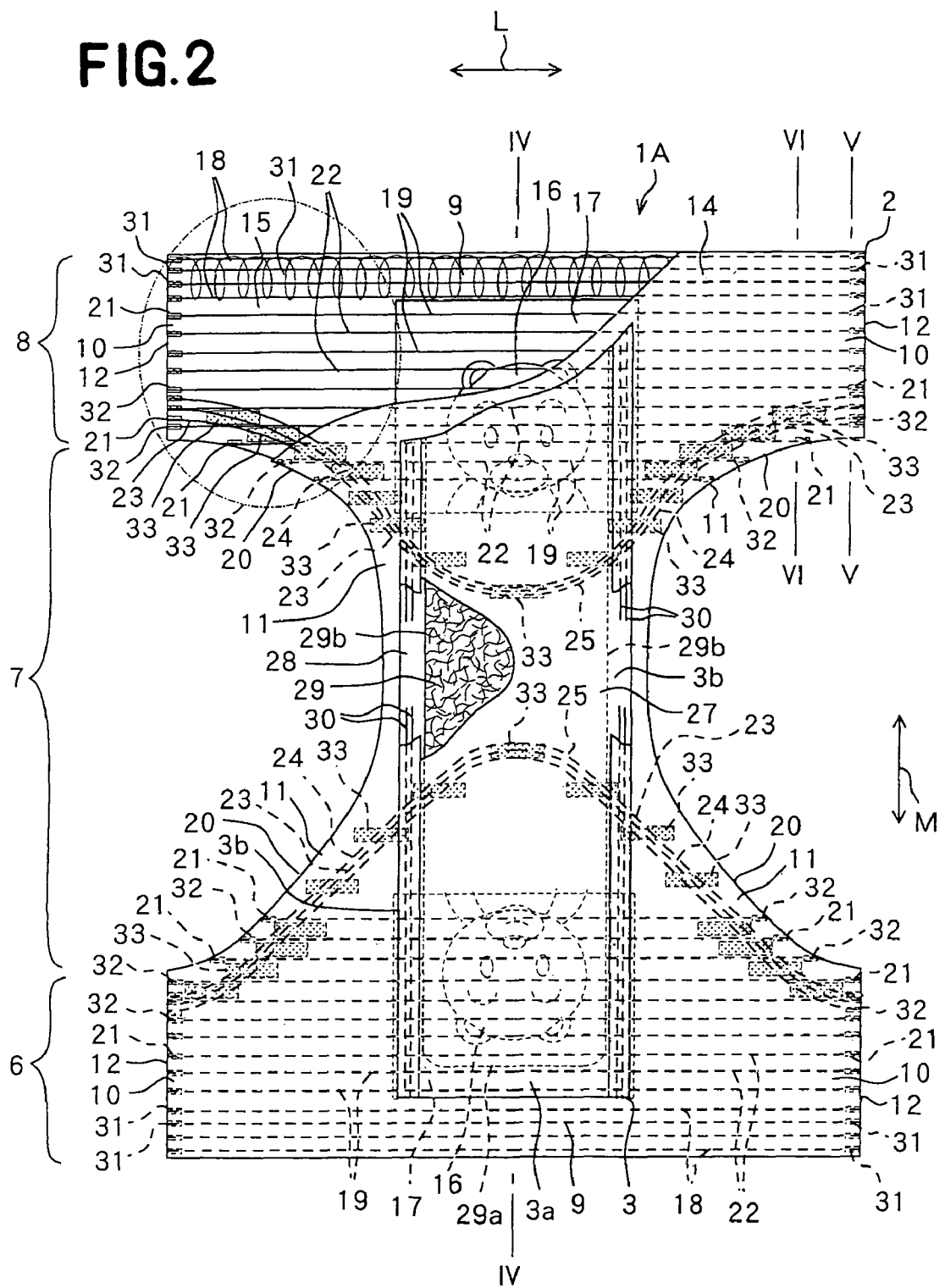
FIG. 2 is a partially cut away developed plan view showing the article of FIG. 1 as before waist lateral zones are connected together.
Figure 3:
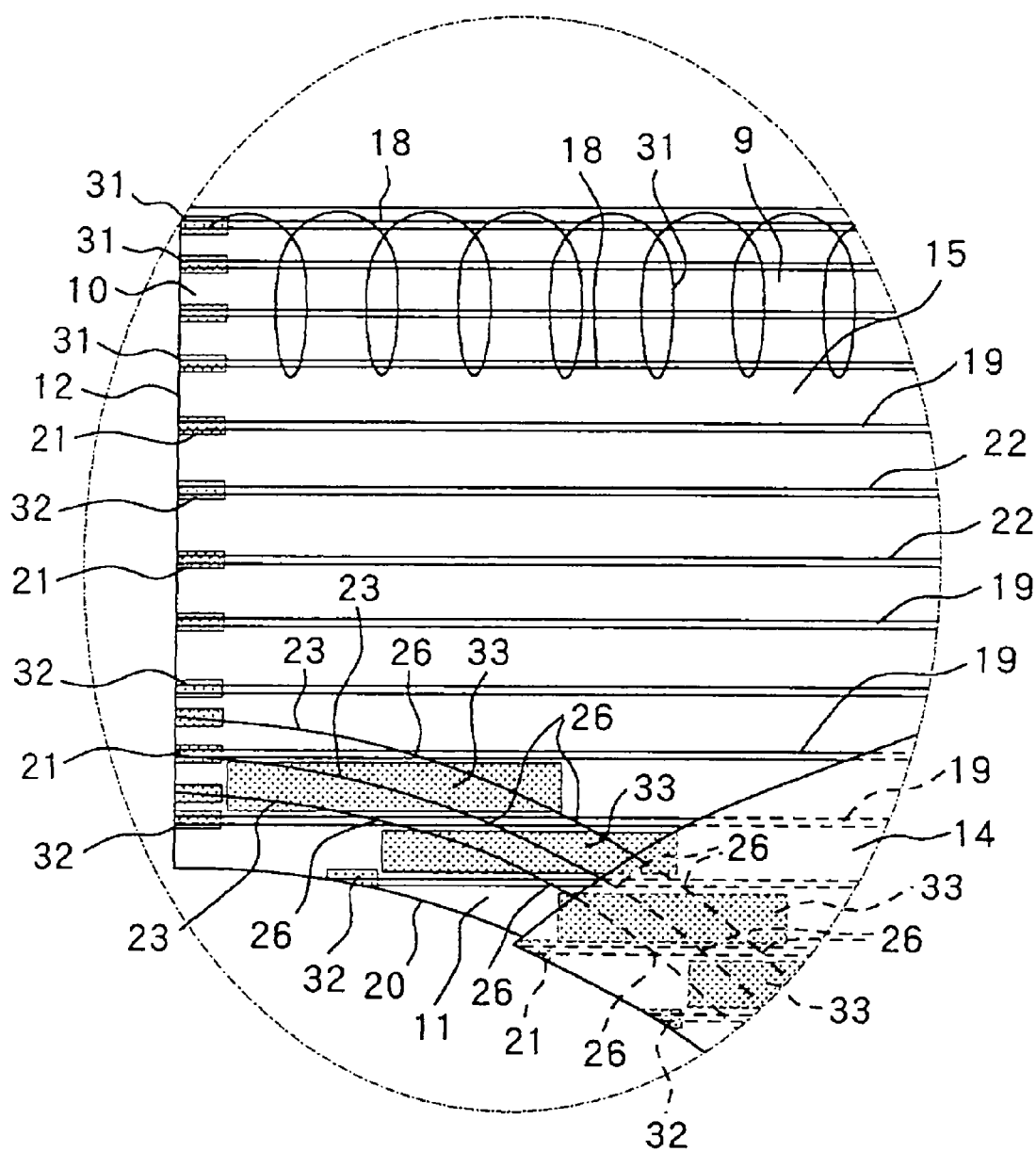
FIG. 3 is a scale-enlarged plan view partially showing a waist region lateral zone and a crotch lateral zone.

FIG. 1 is a perspective view showing a wearing article 1A according to one embodiment of the invention, FIG. 2 is a partially cut away developed plan view showing the article 1A of FIG. 1 as before waist lateral zones 10 are connected together and FIG. 3 is a scale-enlarged plan view partially showing the waist lateral zone 10 and a leg-surrounding zone 11. In FIGS. 1 and 2, a transverse direction is indicated by an arrow L, a longitudinal direction is indicated by an arrow M and a leg-surrounding direction is indicated by an arrow N (in FIG. 1 alone). FIG. 2 shows the article 1A as has been stretched in the transverse direction and in the longitudinal direction. The term used herein "inner surfaces" of respective sheets 14, 15, 27, 28 which will be described in detail refers to the respective surfaces facing a cote 29 and the term used herein "outer surfaces" of respective sheets 14, 15, 27, 28 refers to the respective surfaces facing away from the core 29.

The article 1A comprises a liquid-impervious base sheet 2, a liquid-absorbent panel 3 attached to the inner side of the base sheet 2 and respective elastic members 18, 19, 23, 30. The article 1A is of a so-called pants-type and has a waist-hole 4 and a pair of leg-holes 5.

The base sheet 2 defines front and rear waist regions 6, 8 opposed to each other and a crotch region 7 extending between these waist regions 6, 8. The base sheet 2 has a pair of waist-surrounding upper end zones 9 extending across the front and rear waist regions 6, 8 outside longitudinally opposite ends 3a of the panel 3 in the transverse direction, waist lateral zones 10 extending in the front and rear waist regions 6, 8 outside transversely opposite side edges 3b of the panel 3, and crotch lateral zones 11 extending outside the side edges 3b of the panel 3 in the leg-surrounding direction. The crotch lateral zones 11 describe circular arcs which are convex inward as viewed in the transverse direction of the article 1A. As shown by FIG. 2, the base sheet 2 has a generally hourglass-like planar shape. The base sheet 2 is put flat together along the waist' lateral zones 10 and joined together in the vicinity of edges 12 thereof by means of a plurality of welding lines 13 arranged intermittently in the longitudinal direction.

The base sheet 2 comprises a first sheet 14 lying on the side of the panel 3 and a second sheet 15 lying outside the first sheet 14. The first sheet 14 is formed from a breathable liquid-impervious plastic film and the second sheet 15 is formed from a hydrophobic fibrous nonwoven fabric. A pair of plastic film layers 17 each printed with illustration of a bear's head 16 are attached to the inner surface of the second sheet 15. These film layers 17 are placed in a transverse middle of the front waist region 6 and a transverse middle of the rear waist region 8.

The waist-surrounding upper end zone 9 is provided with a plurality of waist-surrounding first elastic members 18 spaced apart one from another in the longitudinal direction and extending in the transverse direction. The first elastic members 18 are stretched at a predetermined ratio in the transverse direction and attached in such a stretched state to the base sheet 2. In other words, these elastic members 18 are contractible along the waist-surrounding upper end zone 9 in the transverse direction.

Below the first elastic members 18, a plurality of waist-surrounding second elastic members 19 extend in the transverse direction. The second elastic members 19 are spaced apart one from another in the longitudinal direction from the front and rear waist regions toward the crotch region 7. The second elastic members 19 are stretched at a predetermined ratio in the transverse direction and secured in such a stretched state to the base sheet in the front and rear waist regions 6, 8 and a partial range of the crotch region 7 lying aside toward the front and rear waist regions 6, 8. In other words, these second elastic members 19 are contractible in the transverse direction. Each of the second elastic members 19 has transversely opposite the fixed portions 21 secured to the waist lateral zones 10 in the vicinities of the edges 12 thereof and to the crotch lateral zones 11 in the vicinities of the edges 20 thereof and a free portion 22 extending in the transverse direction between the opposite fixed portions 21 across the panel 3 and secured neither to the base sheet 2 nor to the panel 3. The second elastic members 19 extending in the front and rear waist regions 6, 8 contract to a transverse dimension which is the same as or slightly larger than a transverse dimension of the panel 3 lying in the front and rear waist regions as measured between the opposite side edges 3b.

The crotch lateral zones 11 are provided with a plurality of leg-surrounding elastic members 23 arranged to be spaced apart one from another by a predetermined dimension in the transverse direction and extending in the leg-surrounding direction. These leg-surrounding elastic members 23 are stretched in the leg-surrounding direction at a predetermined ratio and secured in such a stretched state to the base sheet 2. In other words, these leg-surrounding elastic members 23 are contractible along the crotch lateral zones 11 in the leg-surrounding direction. The leg-surrounding elastic members 23 comprise leg-surrounding first elastic members 23 extending from the front waist region 6 toward the crotch region 7, generally describing a U-curve relative to the longitudinal direction and leg-surrounding second elastic members 23 extending from the rear waist region 8 toward the crotch region 7, generally describing a U-curve relative to the longitudinal direction. Each of these elastic members 23 has longitudinally opposite lateral portions 24 extending along the crotch lateral zone 11 and a middle portion 25 extending between the lateral portions 24 across the crotch region 7 in the transverse direction.

In the crotch lateral zones 11 and in the lower areas of the respective waist lateral zones 10 placed aside toward the crotch region 7, the free portions 22 of the respective waist-surrounding second elastic members 19 three-dimensionally intersect the leg-surrounding elastic members 23. At the crossover points 26 (See FIG. 3) of the second elastic members 19 and the leg-surrounding elastic members 23, these elastic members 19, 23 are not secured one to another, i.e., let free one from another. The fixed portions 21 of the second elastic members 19 extending across the crotch region 7 lie aside toward the edges 20 of the crotch lateral zones 11 relative to the leg-surrounding elastic members 23.

The panel 3 comprises a liquid-pervious upper layer sheet 27 facing the wearer's skin, a liquid-impervious lower layer sheet 28 facing away from the wearer's skin and a liquid-absorbent core 29 interposed between these upper and lower layer sheets 27, 28. The panel 3 has a generally rectangular planar shape and extends over the crotch region 7 and further into the front and rear waist regions 6, 8. Longitudinally opposite end zones 3a of the panel 3 are defined by portions of the upper and lower layer sheets 27, 28 extending outward beyond the longitudinally opposite ends 29a of the core 29 in the longitudinal direction and transversely opposite lateral zones 3b of the panel 3 are defined by portions of the upper and lower layer sheets 27, 28 extending outward beyond the transversely opposite side edges 29b of the core 29 in the transverse direction. In the end zones 3a and the lateral zones 3b, the upper and lower layer sheets 27, 28 are put flat together and the inner surfaces of these sheets 27, 28 are joined to each other by means of adhesives (not shown). The core 29 is joined to the inner surfaces of the upper and lower layer sheets 27, 28 by means of adhesives (not shown).

In the panel 3, the lateral zones 3b are folded inwardly as viewed in the transverse direction onto the upper surface of the core 29 and joined to the end zones 3a by means of adhesives (not shown). The lateral zones 3b are provided with elastic members 30 extending in the longitudinal direction. These elastic members 30 are stretched in the longitudinal direction at a predetermined ratio and secured in such a stretched state to the respective lateral zones 3b. In other words, these elastic members 30' are contractible in the longitudinal direction. The elastic members 30 are interposed between the upper and lower layer sheets 27, 28 and secured to the inner surfaces of these sheets 27, 28 by means of adhesives (not shown).

To obtain the pants-type article of FIG. 1 from the state shown in FIG. 2, the crotch region 7 is curved with the panel 3 inside, then the lateral zones 10 of the front and rear waist regions 6, 8 are placed one upon another and joined together in the vicinities of the side edges 12 of these lateral zones 10 by means of the plural welding lines 13 (See FIG. 1).

Figure 4:
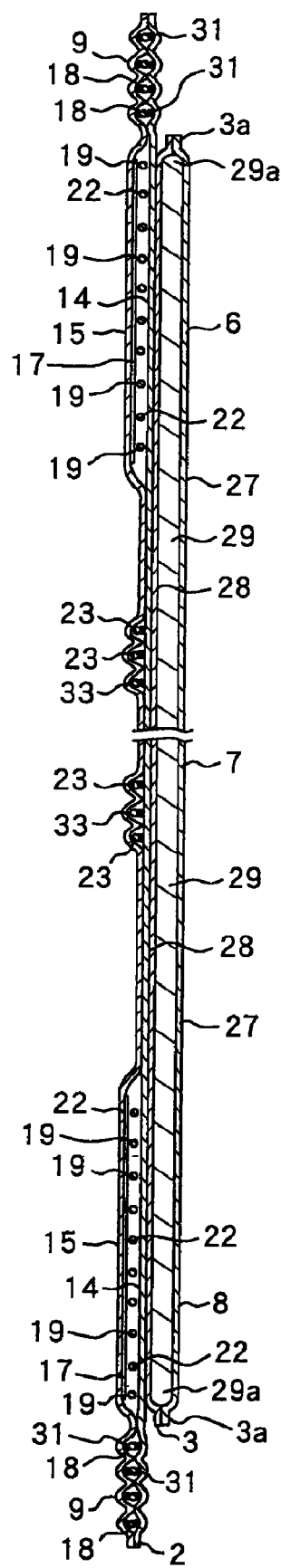
FIG. 4 is a sectional view taken along the line IV-IV in FIG. 2.
Figure 5:
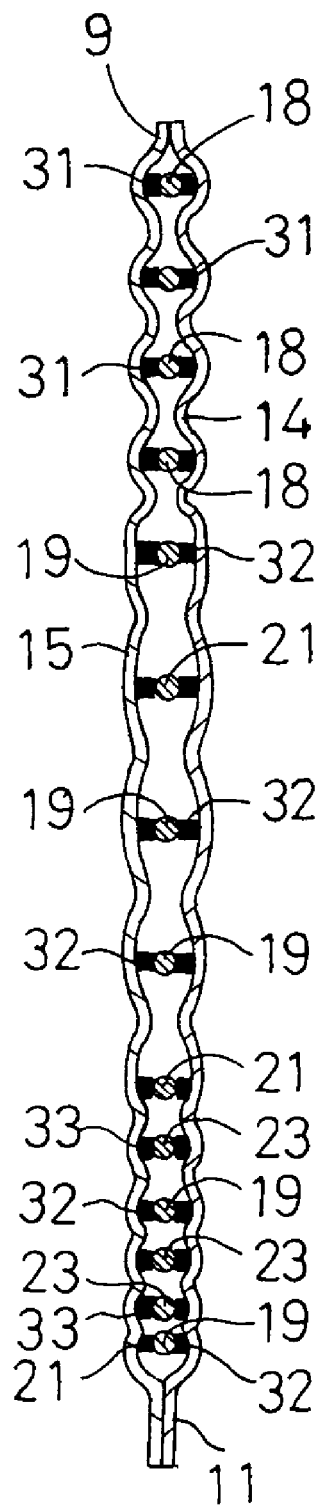
FIG. 5 is a sectional view taken along the line V-V in FIG. 2.
Figure 6:
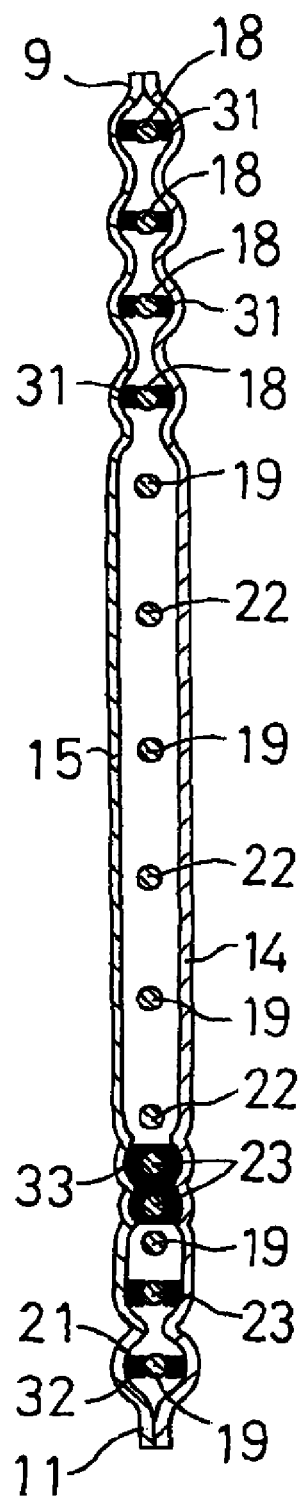
FIG. 6 is a sectional view taken along the line VI-VI in FIG. 2.

FIG. 4 is a sectional view taken along the line IV-IV in FIG. 2, FIG. 5 is a sectional view taken along the line V-V in FIG. 2 and FIG. 6 is a sectional view taken along the line VI-VI in FIG. 2.

In the waist-surrounding upper end zone 9, the waist lateral zones 10 and the crotch lateral zones 11, the inner and outer surfaces of the first and second sheets 14, 15 are intermittently joined together by means of adhesives 31, 32, 33 and, in a longitudinal middle of the crotch region 7, the inner and outer surfaces of these sheets 14, 15 are intermittently joined together by means of adhesives (not shown). Of the panel 3, the outer surface of the lower layer sheet 28 is continuously or intermittently joined to the inner surface of the first sheet 14 by means of adhesives (not shown).

The first elastic members 18 are interposed between the first and second sheets 14, 15 and secured to the inner and outer surfaces of these sheets 14, 15 by means of adhesives 31. The second elastic members 19 are interposed between the first and second sheets 14, 15 and have their fixed portions 21 are secured to the inner and outer surfaces of these sheets 14, 15 by means of adhesives 32. The free portions 22 of the second elastic members 19 are not secured to the first and second sheets 14, 15, i.e., let free from these sheets 14, 15. The leg-surrounding first elastic members 23 and the leg-surrounding second elastic members 23 are interposed between the first and second sheets 14, 15 and secured to the inner and outer surfaces of these sheets 14, 15 by means of adhesives 33.

The second elastic members 19 and the leg-surrounding elastic members 23 are not secured together at the crossover points 26 of these elastic members 19, 23, so there is no anxiety that contraction of the leg-surrounding elastic members 23 might pull the second elastic members 19 in the leg-surrounding direction and thereby might hinder a desired contraction of the second elastic members 19 in the transverse direction. Similarly, there is no anxiety that contraction of the second elastic members 19 might pull the leg-surrounding members 23 in the transverse direction and thereby might hinder a desired contraction of the leg-surrounding elastic members 23 in the leg-surrounding direction.

The leg-surrounding elastic members 23 cooperate with the elastic members 30 along the crotch lateral zones 11 to define generally closed loops adapted to be tightened all around the wearer's thighs. The second elastic members 19 can be sufficiently tightened around the wearer's waist and the leg-surrounding elastic members 23 can be sufficiently tightened around the wearer's thighs to prevent the article 1A from unintentionally slipping down along the wearer's waist, on one hand, and to prevent any quantity of bodily discharges from leaking sideways beyond the crotch lateral zones 11, on the other hand. This is for the reason that, as has been described just above, contraction of the second elastic members 19 and/or the leg-surrounding elastic members 23 never hinders a desired contraction of the leg-surrounding elastic members 23 and/or the second elastic members 19, respectively.

The free portions 22 of the second elastic members 19 are secured neither to the first and second sheets 14, 15 (base sheet 2) nor to the panel 3, so the core 29 is barely affected by a contractile force of the elastic members 19 even when these elastic members 19 contract in the transverse direction. With a consequence, it is not apprehended that the contractile force of the second elastic members 19 might form the core 29 with a plurality of irregular wrinkles and thereby the liquid absorbing function of the core 29 might be deteriorated. It is also not apprehended that a zone of the second sheet 15 in which the free portions 22 of the second elastic members 19 extend might be formed with a plurality of crepe-like wrinkles. In this way, not only touch as well as appearance of the sheet 15 can be improved but also the illustrations 16 can be clearly recognized.

The second elastic members 19 extending in the front and rear waist regions 6, 8 contract to a transverse dimension which is the substantially same as or slightly larger than a transverse dimension of the panel 3 lying in the front and rear waist regions as measured between the opposite side edges 3b, so there is no possibility that the second elastic members 19 might contract to a transverse dimension smaller than that of the panel 3 and consequently might constrine the core 29 in the transverse direction. Such feature can reliably protect the core 29 from being formed with wrinkles.

The fixed portions 21 of the second elastic members 19 extending across the crotch region 7 lie aside toward the edges 20 of the crotch lateral zones 11 relative to the leg-surrounding elastic members 23. Such an arrangement ensures that a contractile force generally over a full length of the second elastic members 19 extending in the crotch region 7 can be utilized to place the panel 3 against the wearer's crotch region and thereby bodily discharges can be reliably absorbed by the panel 3 lying in the crotch region 7.

The elastic members 30 contract inwardly in the longitudinal direction as the article 1A is curved in the longitudinal direction with the panel 3 inside and contractile force of these elastic members 30 bias the lateral zones 3B of the panel 3 to rise on the core 29. Barriers against bodily discharges defined by the lateral zones 3b of the panel 3 rising this manner allows the article 1A to prevent any quantity of bodily discharges from leaking sideways beyond the crotch lateral zones 11.

Figure 7:
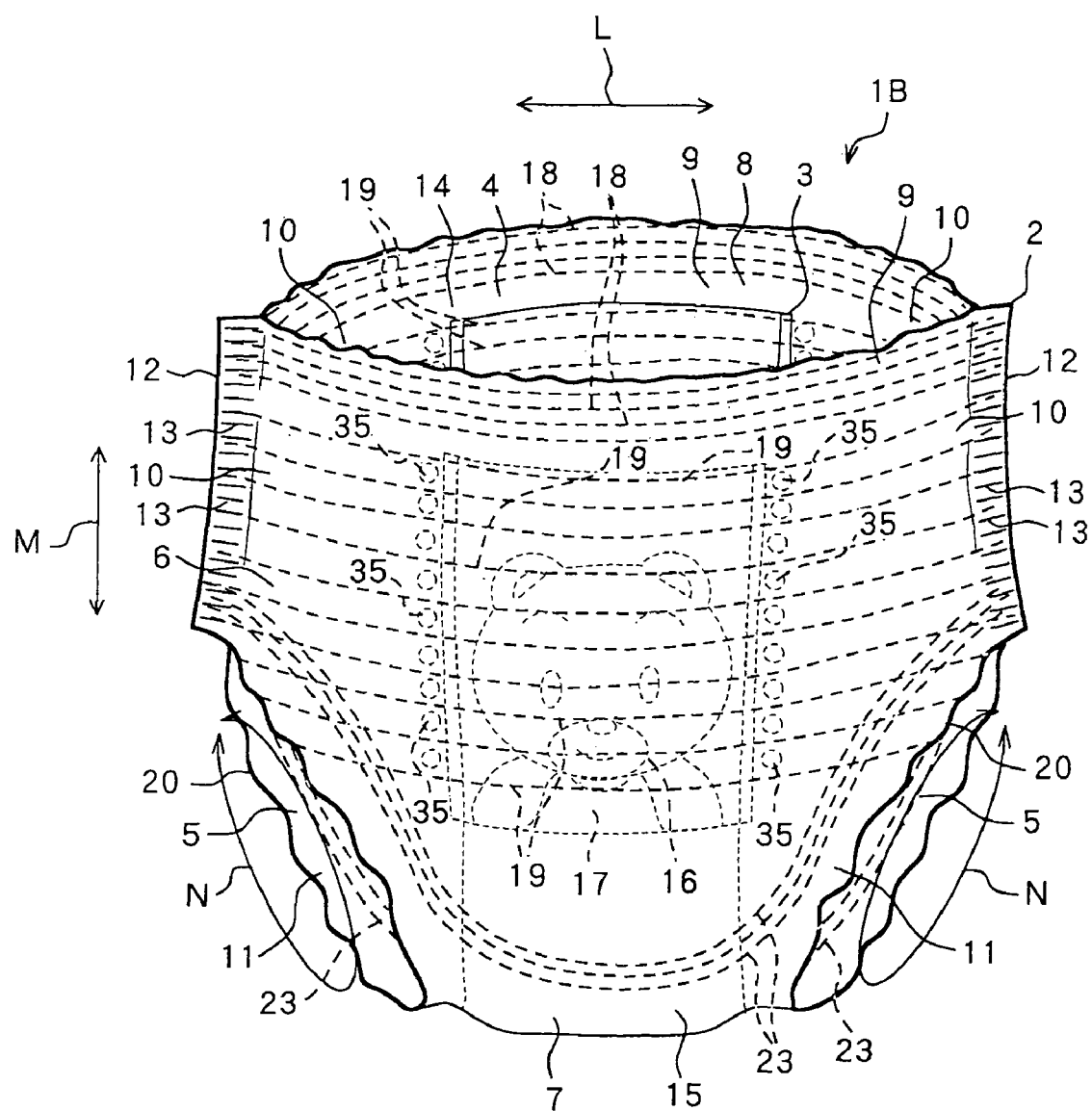
FIG. 7 is a perspective view showing another example of the wearing article.
Figure 8:
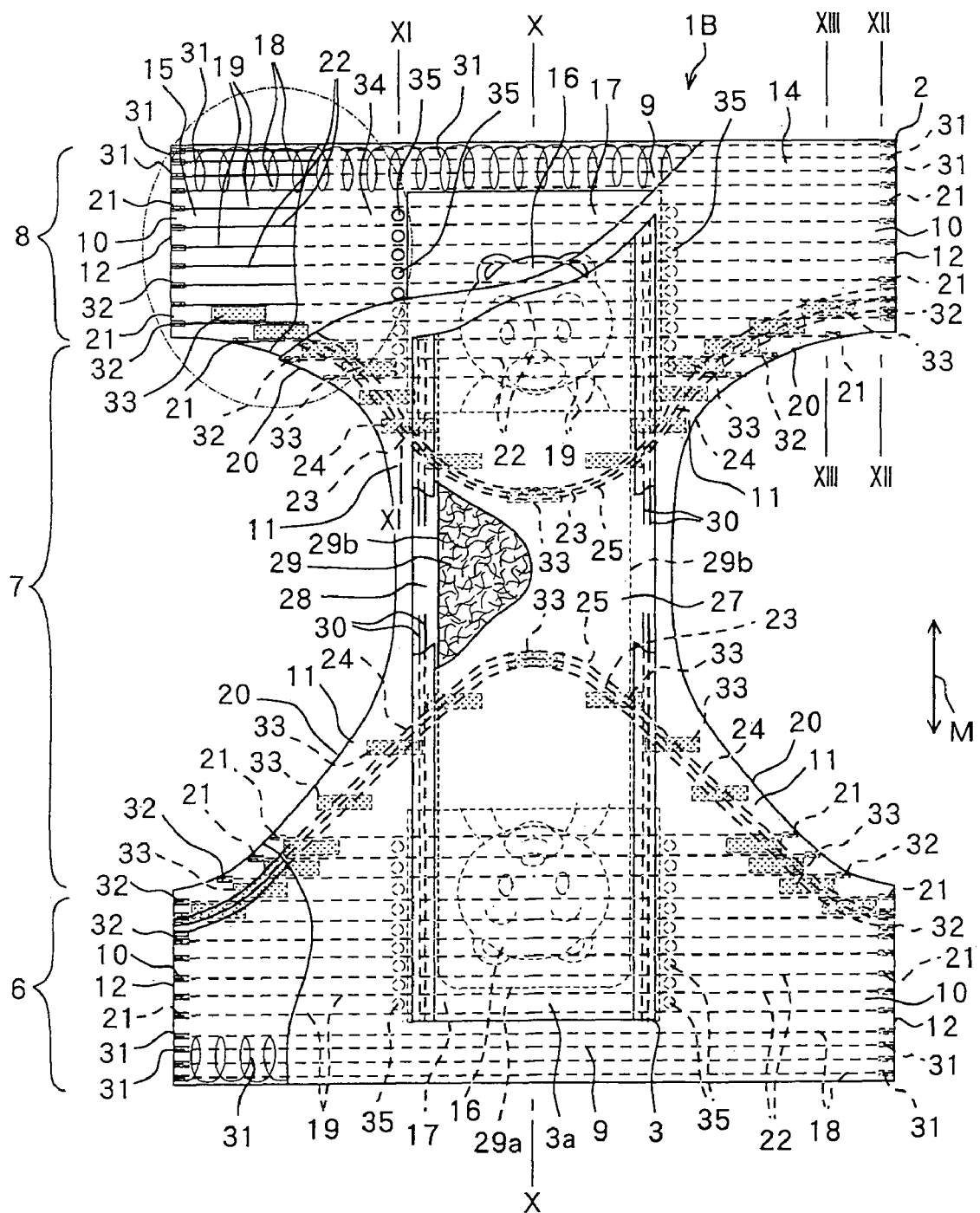
FIG. 8 is partially cut away developed plan view showing the article of FIG. 7 as before waist lateral zones are connected together.
Figure 9:
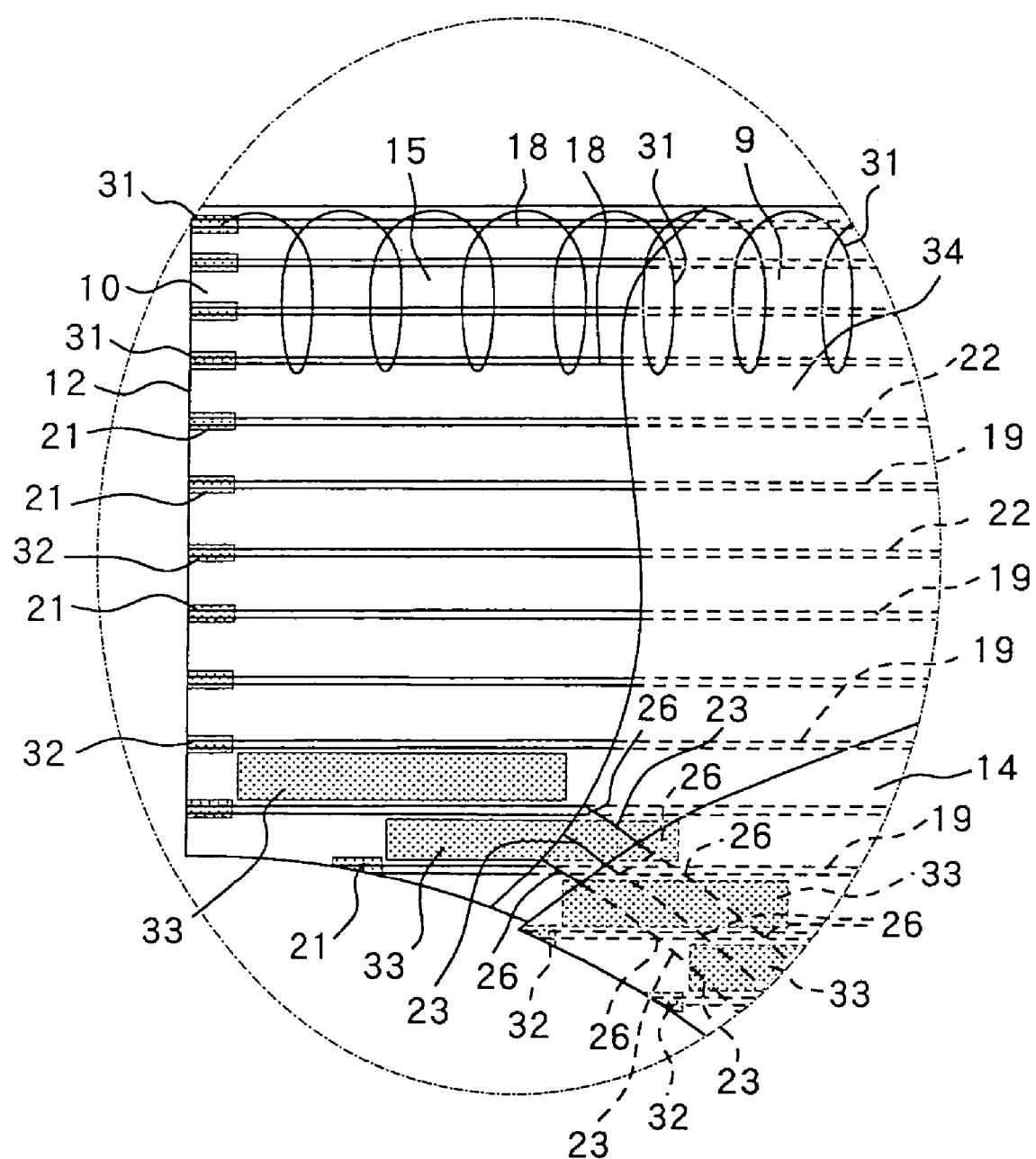
FIG. 9 is a scale-enlarged plan view partially showing a waist lateral zone and a crotch lateral zone.

FIG. 7 is a perspective view showing a wearing article 1B according to another embodiment of the invention, FIG. 8 is partially cut away developed plan view showing the article 1B of FIG. 7 as before waist lateral zones 10 are connected together and FIG. 9 is a scale-enlarged plan view partially showing a waist lateral zone 10 and a crotch lateral zone 11. In FIGS. 7 and 8 also, the transverse direction is indicated by the arrow L, the longitudinal direction is indicated by the arrow M and the leg-surrounding direction is indicated by the arrow N (in FIG. 7 alone). The term used herein "inner surface" of the sheet 34 refers to the surface of the sheet 34 facing the core 29 and the term used herein "outer surface" of the sheet 34 refers to the surface of the sheet 34 facing away from the core 29.

The article 1B comprises a liquid-impervious base sheet 2, a liquid-absorbent panel 3 attached to the inner side of the base sheet 2 and respective elastic members 18, 19, 23, 30. The article 1B is of pants-type and has a waist-hole 4 and a pair of leg-holes 5.

The base sheet 2 defines front and rear waist regions 6, 8 opposed to each other and a crotch region 7 extending between these waist regions 6, 8. The base sheet 2 has a pair of waist-surrounding upper end zones 9 extending across the front and rear waist regions 6, 8 outside longitudinally opposite ends 3a of the panel 3 in the transverse direction, a pair of waist lateral zones 10 extending in the front and rear waist regions 6, 8 outside transversely opposite side edges 3b of the panel 3, and a pair of crotch lateral zones 11 extending outside the side edges 3b of the panel 3 in the leg-surrounding direction. The crotch lateral zones 11 describe circular arcs which are convex inwardly as viewed in the transverse direction of the article 1B. The base sheet 2 is put flat together along the waist lateral zones 10 and joined together in the vicinity of edges 12 thereof by means of a plurality of welding lines 13 arranged intermittently in the longitudinal direction.

The base sheet 2 comprises a first sheet 14 lying on the side of the panel 3, a second sheet 15 lying outside the first sheet 14 and a third sheet 34 interposed between the first and second sheets 14, 15. The first and second sheets 14, 15 are formed from a hydrophobic fibrous nonwoven fabric and the third sheet 34 is formed from a breathable liquid-impervious plastic film. A pair of plastic film layers 17 each printed with illustration of a bear's head 16 are attached to the inner surface of the second sheet 15. These film layers 17 are placed in a transverse middle of the front waist region 6 and a transverse middle of the rear waist region 8.

The waist-surrounding upper end zone 9 is provided with a plurality of waist-surrounding first elastic members 18 spaced apart one from another in the longitudinal direction and extending in the transverse direction. The first elastic members 18 are stretched at a predetermined ratio in the transverse direction and attached in such a stretched state to the base sheet 2. In other words, these elastic members 18 are contractible along the waist-surrounding upper end zone 9 in the transverse direction.

Below the first elastic members 18, a plurality of waist-surrounding second elastic members 19 extend in the transverse direction. The second elastic members 19 are spaced apart one from another in the longitudinal direction from the front and rear waist regions toward the crotch region 7. The second elastic members 19 are stretched at a predetermined ratio in the transverse direction and secured in such a stretched state to the base sheet in the front and rear waist regions 6, 8 and a partial range of the crotch region 7 lying aside toward the front and rear waist regions 6, 8. In other words, these second elastic members 19 are contractible in the transverse direction. Each of the second elastic members 19 has transversely opposite the fixed portions 21 secured to the waist lateral zones 10 in the vicinities of the edges 12 thereof as well as to the crotch lateral zones 11 in the vicinities of the edges 20 thereof and a free portion 22 extending in the transverse direction between the opposite fixed portions 21 across the panel 3 and secured neither to the base sheet 2 nor to the panel 3. The second elastic members 19 extending in the front and rear waist regions 6, 8 contract to a transverse dimension which is the substantially same as or slightly larger than a transverse dimension of the panel 3 lying in the front and rear waist regions as measured between the opposite side edges 3b.

The crotch lateral zones 11 are provided with a plurality of leg-surrounding elastic members 23 arranged to be spaced apart one from another by a predetermined dimension in the transverse direction and extending in the leg-surrounding direction. These leg-surrounding elastic members 23 are stretched in the leg-surrounding direction at a predetermined ratio and secured in such a stretched state to the base sheet 2. In other words, these leg-surrounding elastic members 23 are contractible along the crotch lateral zones 11 in the leg-surrounding direction. The leg-surrounding elastic members 23 comprise leg-surrounding first elastic members 23 and leg-surrounding second elastic members 23. These elastic members 23 have longitudinally opposite lateral portions 24 extending along the crotch lateral zones 11 so as to describe generally U-shaped curves extending from the front and rear waist regions 6, 8 toward the crotch region 7 and middle portions 25 extending between the lateral portions 24 across the crotch region 7 in the transverse direction.

In the crotch lateral zones 11 and in the lower areas of the respective waist lateral zones 10 placed aside toward the crotch region 7, the free portions 22 of the respective waist-surrounding second elastic members 19 three-dimensionally intersect the leg-surrounding elastic members 23. At the crossover points 26 (See FIG. 9) of the second elastic members 19 and the leg-surrounding elastic members 23, these elastic members 19, 23 are not secured one to another, i.e., let free one from another. The fixed portions 21 of the second elastic members 19 extending across the crotch region 7 lie aside toward the edges 20 of the crotch lateral zones 11 relative to the leg-surrounding elastic members 23.

The panel 3 comprises a liquid-pervious upper layer sheet 27 facing the wearer's skin, and a liquid-absorbent core 29 interposed between the upper layer sheet 27 and the first sheet 14. The panel 3 has a generally rectangular planar shape and extends over the crotch region 7 and further into the front and rear waist regions 6, 8. Longitudinally opposite end zones 3a of the panel 3 are defined by a portion of the upper and layer sheets 27 extending outward beyond the longitudinally opposite ends 29a of the core 29 in the longitudinal direction and transversely opposite lateral zones 3b of the panel 3 are defined by a portion of the upper layer sheet 27 extending outward beyond the transversely opposite side edges 29b of the core 29 in the transverse direction. The lateral zones 3b are provided with elastic members 30 extending in the longitudinal direction. The elastic members 30 are stretched in the longitudinal direction at a predetermined ratio and attached in such a stretched state to the lateral zones 3b. In other words, the elastic members 30 are contractible in the longitudinal direction. The elastic members 30 are secured to the sheet 27 by means of adhesive (not shown) in a manner that these elastic members 30 are wrapped with a part of the upper layer sheet 27.

Figure 10:
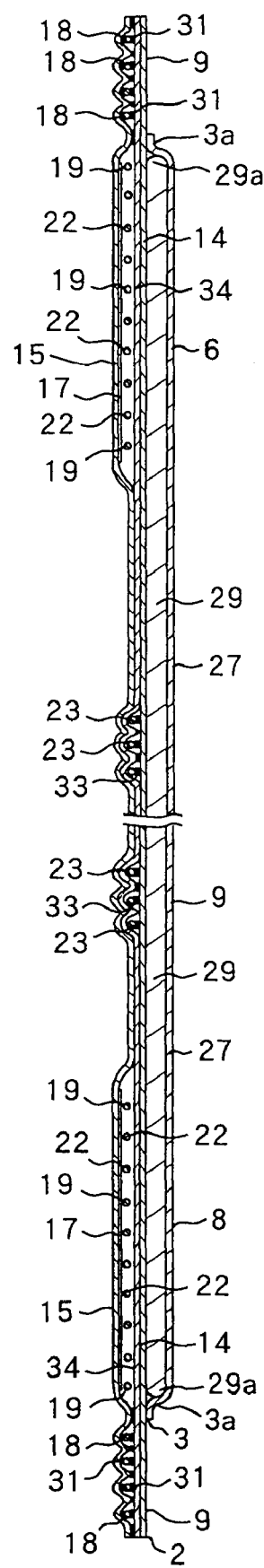
FIG. 10 is a sectional view taken along the line X-X in FIG. 8.
Figure 11:
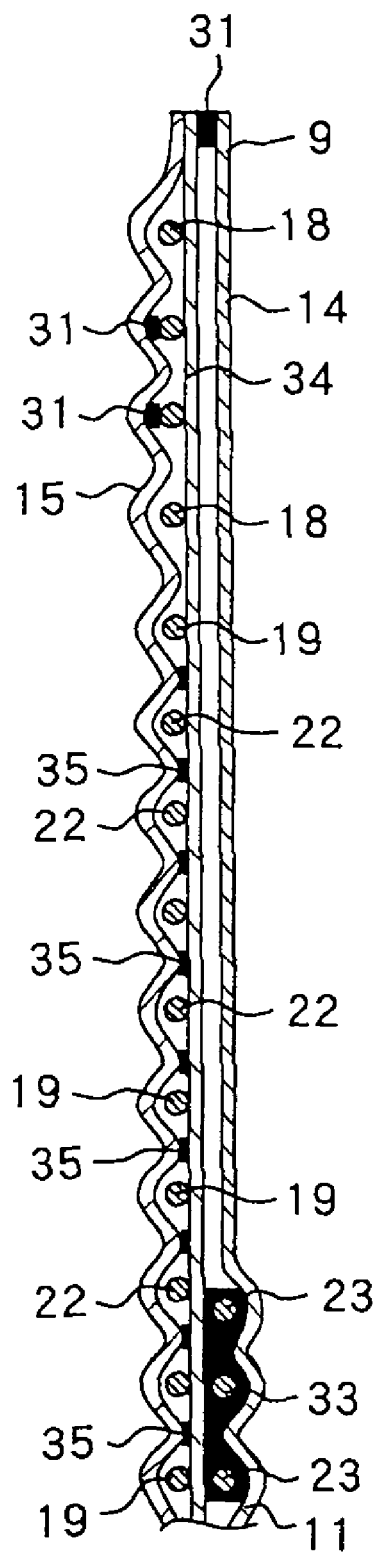
FIG. 11 is a sectional view taken along the line XI-XI in FIG. 8.
Figure 12:
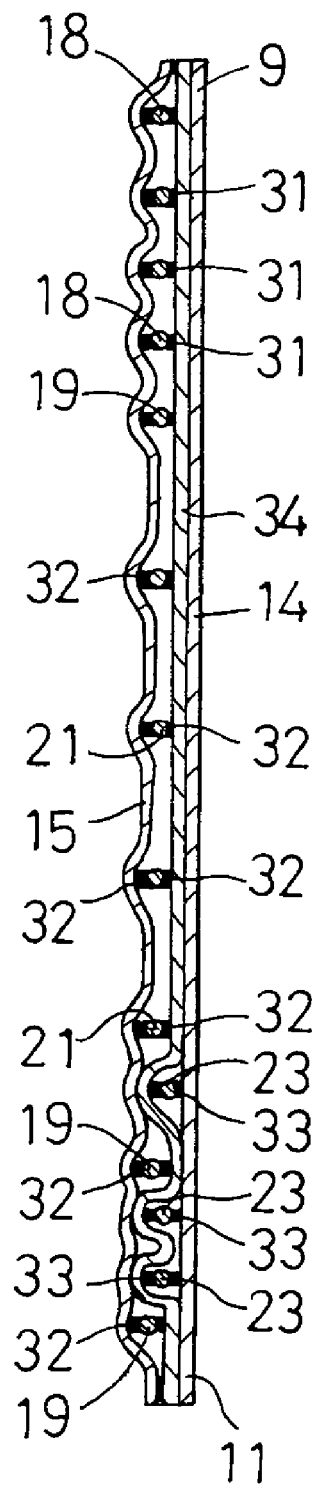
FIG. 12 is a sectional view taken along the line XII-XII in FIG. 8.
Figure 13:
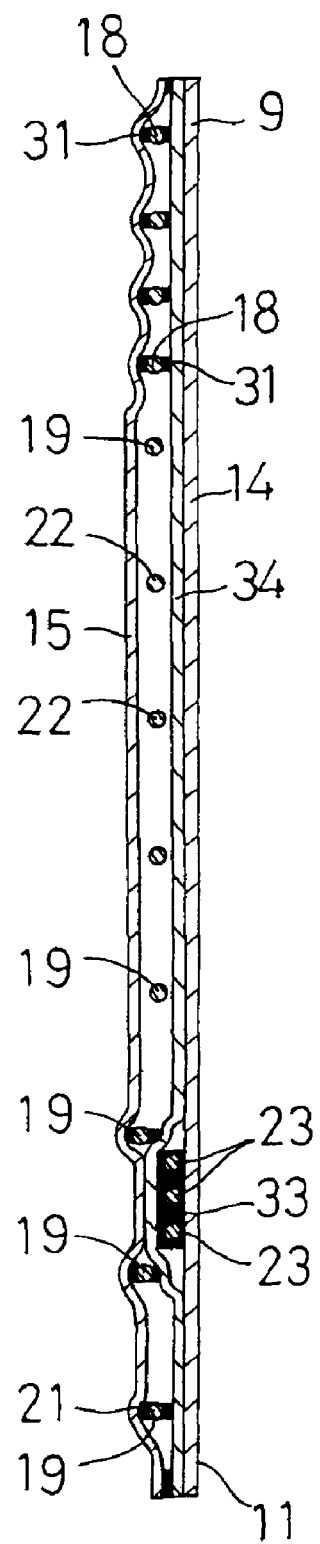
FIG. 13 is a sectional view taken along the line XIII-XIII in FIG. 8.

FIG. 10 is a sectional view taken along the line X-X in FIG. 8, FIG. 11 is a sectional view taken along the line XI-XI in FIG. 8, FIG. 12 is a sectional view taken along the line XII-XII in FIG. 8 and FIG. 13 is a sectional view taken along the line XIII-XIII in FIG. 8.

In the waist-surrounding upper end zone 9, the waist lateral zones 10 and the crotch lateral zones 11, the inner and outer surfaces of the first and second sheets 14, 15 are intermittently joined together by means of adhesives 31, 32, 33 and, in a longitudinal middle of the crotch region 7, the inner and outer surfaces of these sheets 14, 15 are intermittently joined together by means of adhesives (not shown).

In the waist-surrounding upper end zone 9, the waist lateral zones 10 and the crotch lateral zones 11, the inner and outer surfaces of the second and third sheets 15, 34 are intermittently joined together by means of adhesives 31, 32, 33 and, in a longitudinal middle of the crotch region 7, the inner and outer surfaces of these sheets 15, 34 are intermittently joined together by means of adhesives (not shown). The second and third sheets 15, 34 are joined together by means of plural welded spots 35 defined between each pair of the adjacent free portions 22 of the second elastic members 19 and spaced from each other by a predetermined dimension in the longitudinal direction. The welded spots 35 are formed by intermittently welding these sheets 15, 34 to each other immediately outside the respective lateral zones 3b of the panel 3.

In the end zones 3a and the lateral zones 3b of the panel 3, the inner surface of the upper layer sheet 27 is joined to the inner surface of the first sheet 14 by means of adhesives (not shown) and the lower surface of the core 29 is joined to the inner surface of the first sheet 14 by means of adhesives (not shown). The upper surface of the core 29 is joined to the inner surface of the upper layer sheet 27 by means of adhesives (not shown).

The first elastic members 18 are interposed between the second and third sheets 15, 34 and secured to the inner and outer surfaces of these sheets 15, 34 by means of adhesives 31. The second elastic members 19 are interposed between the second and third sheets 15, 34 and have their fixed portions 21 secured to the inner and outer surfaces of these sheets 15, 34 by means of adhesives 32. The free portions 22 of the second elastic members 19 are not secured to the second and third sheets 15, 34, i.e., let free from these sheets 15, 34. The leg-surrounding first elastic members 23 and the leg-surrounding second elastic members 23 are interposed between the first and third sheets 14, 34 and secured to the inner and outer surfaces of these sheets 14, 34 by means of adhesives 33. The second elastic members 19 and the leg-surrounding elastic members 23 are spaced apart one from another with the third sheet 34 lying therebetween.

The second elastic members 19 and the leg-surrounding elastic members 23 are not secured together at the crossover points 26 of these elastic members 19, 23, so there is no anxiety that contraction of the leg-surrounding elastic members 23 might pull the second elastic members 19 in the leg-surrounding direction and thereby might hinder a desired contraction of the second elastic members 19 in the transverse direction. Similarly, there is no anxiety that contraction of the second elastic members 19 might pull the leg-surrounding members 23 in the transverse direction and thereby might hinder a desired contraction of the leg-surrounding elastic members 23 in the leg-surrounding direction.

The leg-surrounding elastic members 23 cooperate with the elastic members 30 along the crotch lateral zones 11 to define generally closed loops adapted to be tightened all around the wearer's thighs. The second elastic members 19 can be sufficiently tightened around the wearer's waist and the leg-surrounding elastic members 23 can be sufficiently tightened around the wearer's thighs to prevent the article 1B from unintentionally slipping down along the wearer's waist, on one hand, and to prevent any quantity of bodily discharges from leaking sideways beyond the crotch region's lateral zones 11, on the other hand. This is for the reason that, as has been described just above, contraction of the second elastic members 19 and/or the leg-surrounding elastic members 23 never hinders a desired contraction of the leg-surrounding elastic members 23 and/or the second elastic members 19, respectively.

The second elastic members 19 and the leg-surrounding elastic members 23 are spaced apart one from another with the third sheet 34 lying therebetween so that the third sheet 34 may appropriately limit the contractile force of the leg-surrounding elastic members 23 acting on the second elastic members 19 as well as the contractile force of the second elastic members 19 acting on the leg-surrounding elastic members 23. Thus it is reliably ensured to prevent the contractile force of the elastic members 19 and/or 23 from interfering with the desired contraction of the other elastic members 23 and/or 19, respectively.

The free portions 22 of the second elastic members 19 are secured neither to the second and third sheets 15, 34 (base sheet 2) nor to the panel 3, so the core 29 is barely affected by a contractile force of the elastic members 19 even when these elastic members 19 contract in the transverse direction. With a consequence, it is not apprehended that the contractile force of the second elastic members 19 might form the core 29 with a plurality of irregular wrinkles and thereby the liquid absorbing function of the core 29 might be deteriorated. It is also not apprehended that a zone of the second sheet 15 in which the free portions 22 of the second elastic members 19 extend might be formed with a plurality of crepe-like wrinkles. In this way, not only touch as well as appearance of the sheet 15 can be improved but also the illustrations 16 can be free from distortion and clearly recognized.

The second elastic members 19 extending in the front and rear waist regions 6, 8 contract to a transverse dimension which is substantially the same as or slightly larger than a transverse dimension of the panel 3 lying in the front and rear waist regions as measured between the opposite side edges 3b, so there is no possibility that the second elastic members 19 might contract to a transverse dimension smaller than that of the panel 3 and consequently might constringe the core 29 in the transverse direction. Such a feature can reliably protect the core 29 from being formed with wrinkles.

The second sheet 15 and the third sheet 34 between which the second elastic members 19 are interposed are intermittently secured together by means of the welded spots 35 and therefore a displacement of the free portions of the second elastic members 19 in the longitudinal direction is reliably prevented by these welded spots 35 even if the movement of the wearer's body is transmitted to the second elastic members 19. In this way, it is not apprehended that the free portions 22 might shift in the longitudinal direction and these free portions 22 normally spaced apart one from another in the longitudinal direction might get together.

The fixed portions 21 of the second elastic members 19 extending across the crotch region 7 lie aside toward the edges 20 of the crotch lateral zones 11 relative to the leg-surrounding elastic members 23. Such an arrangement ensures that a contractile force generally over a full length of the second elastic members 19 extending in the crotch region 7 can be utilized to place the panel 3 against the wearer's crotch region and thereby bodily discharges can be reliably absorbed by the panel 3 lying in the crotch region 7.

Figure 14:
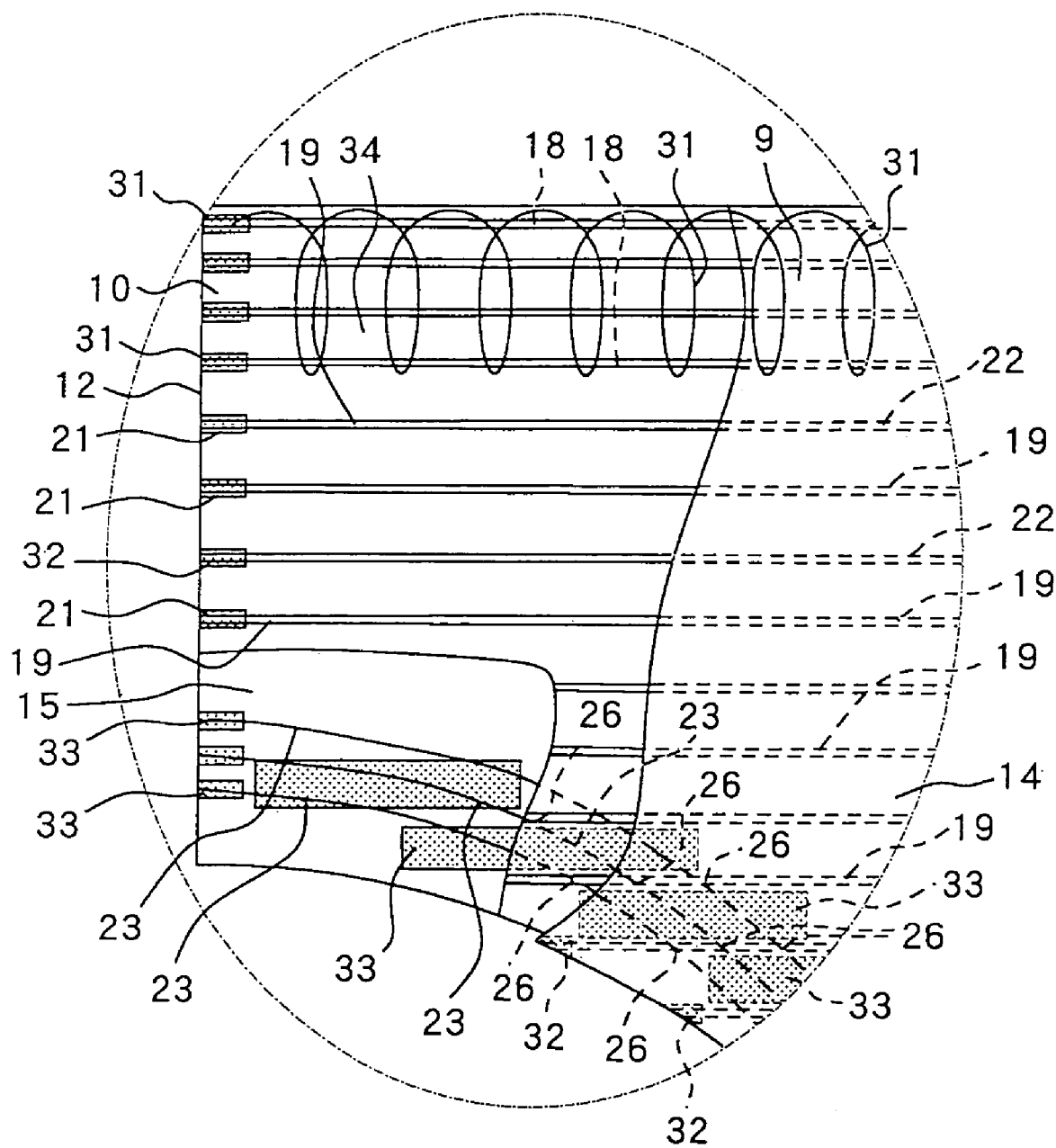
FIG. 14 is a view similar to FIG. 9, partially showing a waist lateral zone and a crotch lateral zone in an enlarged scale.
Figure 15:
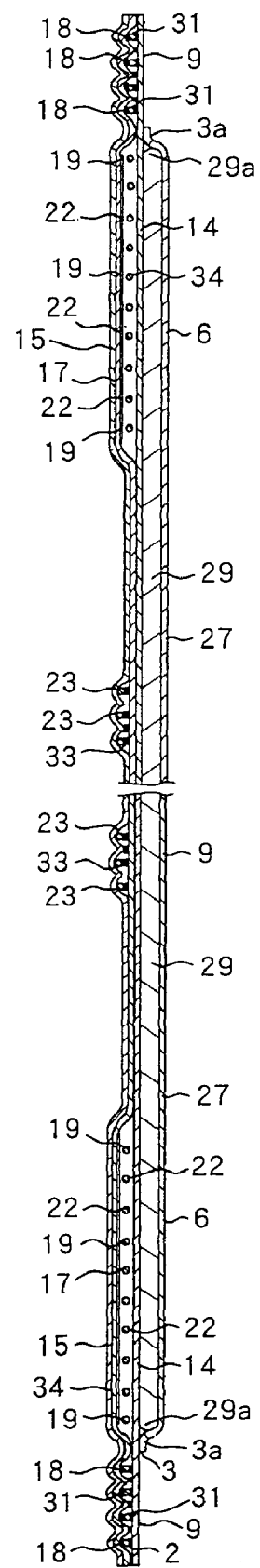
FIG. 15 is a sectional view of the article taken along the same line as in FIG. 10.

It is also possible without departing from the scope of the invention to provide an alternative arrangement such that the first elastic members 18 as well as the second elastic members 19 are interposed between the first sheet 14 and the third sheet 34 and the leg-surrounding elastic members, 23 are interposed between the second sheet 15 and the second sheet 34 as shown in FIGS. 14 and 15. FIG. 14 is a view similar to FIG. 9, partially showing a waist lateral zone 10 and a crotch lateral zone 11 in an enlarged scale and FIG. 15 is a sectional view of the article 1B taken along the same line as in FIG. 10. In the arrangement shown in FIGS. 14 and 15, the first elastic members 18 are bonded to the inner and outer surfaces of the sheets 14, 34, respectively, by means of adhesives 31, the fixed portions 21 of the second elastic members 19 are secured to the inner and outer surfaces of these sheets 14, 34, respectively, by means of adhesives 32 and the leg-surrounding first elastic members 23 as well as the leg-surrounding second elastic members 23 are secured to the inner and outer surfaces of the sheets 15, 34, respectively, by means of adhesives 33. The free portions 22 of the second elastic members 19 are secured neither to the first sheet 14 nor to the third sheet 34, i.e., let free from these sheets 14, 34. The second elastic members 19 and the leg-surrounding elastic members 23 are spaced apart one from another with the third sheet 34 lying therebetween.

In these articles 1A, 1B illustrated as specific embodiments, it is possible without departing from the scope of the invention to arrange the waist-surrounding second elastic members 19 to be spaced apart from any one of the front and rear waist regions 6, 8 toward the crotch region 7 by a predetermined dimension in the longitudinal direction. The article 1A shown in FIG. 1 may be constructed similarly to the article 1B shown in FIG. 7 in that the first and second sheets 14, 15 are joined together by means of a plurality of welded spots 35 lying between each pair of the adjacent free portions of the second elastic members 19 so as to be spaced apart one from another by a predetermined dimension in the longitudinal direction.

In the article 1B shown in FIG. 7, it is possible without departing from the scope of the invention to interpose the first and second elastic members 18, 19 as well as the leg-surrounding elastic members 23 between the first and third sheets 14, 34 or to interpose the first and second elastic members 18, 19 as well as the leg-surrounding elastic members 23 between the second and third sheets 15, 34. When the second elastic members 19 are interposed between the first and third sheets 14, 34, the first and third sheets 14, 34 may be joined together by means of a plurality of welded spots 35 lying between each pair of the adjacent free portions 22 of the second elastic members 19 so as to be spaced apart one from another by a predetermined dimension in the longitudinal direction. It is possible without departing from the scope of the invention to join the first, second and third sheets 14, 15, 34 together by means of the welded spots 35 and/or to form the welded spots 35 not only in the vicinities of the lateral zones 3b of the panel 3 but also over generally entire ranges of the respective waist lateral zones 10.

Stock materials for the upper layer sheet 27 may be selected from a hydrophilic fibrous nonwoven fabric, a hydrophobic fibrous nonwoven fabric having a plurality of apertures and a plastic film having a plurality of fine apertures. Stock materials for the lower layer sheet 28 may be selected from a hydrophobic fibrous nonwoven fabric and a breathable liquid-impervious plastic film. It is possible to use a composite sheet comprising a hydrophobic fibrous nonwoven fabric and a breathable liquid-impervious plastic film laminated upon each other as stock materials for the first through third sheets 14, 15, 34 and the lower layer sheet 28. It is also possible to use a spun bond fibrous nonwoven fabric having a high strength and a desired flexibility laminated upon at least one side of a melt blown fibrous nonwoven fabric having a high water-resistance.

The nonwoven fabric may be selected from those made by spun lace-, needle punch-, melt blown-, thermal bond-, spun bond- and chemical bond-processes. The component fibers may be selected from a group consisting of polyolefin-, polyester- and polyamide-based fibers and sheath-and-core type conjugate fiber or side-by-side type conjugate fibers of polyethylene/polypropylene or polyethylene/polyester.

The core 29 comprises a mixture of fluff pulp and superabsorbent polymer particles or a mixture of fluff pulp, superabsorbent polymer particles and thermoplastic synthetic resin fibers, in any case, compressed to a desired thickness. Preferably, the core 29 is entirely wrapped with a liquid-pervious sheet such as a tissue paper or a hydrophilic fibrous nonwoven fabric in order to prevent the core 29 from getting out of its initial shape and to prevent the polymer particles from falling off. Adhesives 31, 32, 33 may be selected from a group consisting of hot melt adhesives, acrylic adhesives and rubber-based adhesives.

Joining of the sheets 15, 14, 27, 28, 34 to one to another, joining of the core 29 to the sheets 27, 28 and securing of the elastic members 18, 19, 23, 30 to the sheets 15, 14, 27, 28, 34 may be achieved by using not only adhesives but also welding techniques such as heat-sealing or sonic sealing techniques.

The pants-type disposable wearing article according to the present invention is primarily characterized in that the second elastic members and the leg-surrounding elastic members are not secured together at the crossover points of these elastic members. This feature eliminates an anxiety that contraction of the second elastic members and might mutually interfere with a desired contraction of the leg-surrounding elastic members and the second elastic members, respectively. With the article put on the wearer, the second elastic members can be sufficiently tightened around the wearer's waist and the leg-surrounding elastic members can be sufficiently tightened around the wearer's thighs to prevent the article from unintentionally slipping down along the wearer's waist, on one hand, and to prevent any quantity of bodily discharges from leaking sideways beyond the crotch lateral zones, on the other hand. In this article, the free portions of the second elastic members are secured neither to the base-sheet nor to the panel, so the core is barely affected by a contractile force of the elastic members even when these elastic members contract in the transverse direction. With an advantageous consequence, it is not apprehended that the contractile force of the second elastic members might form the core with a plurality of irregular wrinkles and thereby the liquid absorbing function of the core might be deteriorated.

In the case of the embodiment in which the fixed portions of the second elastic members extending across the crotch region lie aside toward the edges of the crotch lateral zones relative to the leg-surrounding elastic members, a contractile force substantially over a full length of the second elastic members extending in the crotch region can be utilized to place the panel against the wearer's crotch region and thereby bodily discharges can be reliably absorbed by the panel lying in the crotch region.

In the case of the embodiment in which the second elastic members extending in the front and rear waist regions contract to a transverse dimension which is substantially the same as or slightly larger than a transverse dimension of the panel lying in the front and rear waist regions as measured between the opposite side edges, there is no possibility that the second elastic members might contract to a transverse dimension smaller than that of the panel and consequently might constringe the core in the transverse direction. Such a feature can reliably protect the core from being formed with wrinkles.

In the case of the embodiment in which the second elastic members and the leg-surrounding elastic members are spaced one from another with the third sheet forming the base sheet lying therebetween, the third sheet appropriately limits the contractile force of the leg-surrounding elastic members acting on the second elastic members as well as the contractile force of the second elastic members acting on the leg-surrounding elastic members. Thus it is reliably ensured to prevent the contractile force of these elastic members from mutually interfering with the desired contraction of the respective elastic members.

In the case of the embodiment in which the second sheet and the third sheet between which the second elastic members are interposed are intermittently secured together by means of the welded spots, a displacement of the free portions of the second elastic members in the longitudinal direction is reliably prevented by these welded spots even if the movement of the wearer's body is transmitted to the second elastic members. In this way, it is not apprehended that the free portions might shift in the longitudinal direction and these free portions normally spaced one from another in the longitudinal direction might get together.

What is claimed is:

1. A pants-type disposable wearing article, comprising:
   a liquid-impervious base sheet defining front and rear waist regions opposed to each other and a crotch region extending in a longitudinal direction of said article between said front and rear waist regions;
   a liquid-absorbent panel extending over said crotch region and further into said front and rear waist regions;
   said base sheet having, in said front and rear waist regions, a waist-surrounding end zone extending in a transverse direction of said article, a pair of waist lateral zones extending in the longitudinal direction and, in said crotch region, a pair of crotch lateral zones extending in leg-surrounding directions, respectively;
   said base sheet being provided with
      a waist-surrounding first elastic member extending in the transverse direction along said waist-surrounding end zone and being contractible in said transverse direction,
      a plurality of waist-surrounding second elastic members lying below said first elastic members and being contractible in said transverse direction, and
      a plurality of leg-surrounding elastic members extending along said crotch lateral zones in the leg-surrounding directions, respectively, and being contractible in said leg-surrounding directions, respectively;
   said second elastic members being located in said crotch region and at least one of said front and rear waist regions and spaced apart one from another by a predetermined interval in said longitudinal direction; and said waist lateral zones being connected together to form a waist-hole and a pair of leg-holes;
wherein
each of said second elastic members has
fixed end portions secured to said waist lateral zones and said crotch lateral zones in vicinities of respective side edges of said lateral zones, and
a free middle portion connecting and extending between said fixed end portions across said panel in said transverse direction and being directly secured neither to said base sheet nor to said panel; and
said free middle portions of said second elastic members and said leg-surrounding elastic members cross, without intersecting, one another in at least said crotch lateral zones and are not secured together at their crossing points;
said base sheet comprises a first sheet and a second sheet, said first sheet being sandwiched between said panel and said second sheet; and
said first and second elastic members as well as said leg-surrounding elastic members are interposed between said first sheet and said second sheet.

2. The wearing article according to claim 1, wherein:
said base sheet has a third sheet interposed between said first sheet and said second sheet;
said second elastic members are interposed between said first and third sheets or between said second and third sheets;
said leg-surrounding elastic members are interposed between the pair of sheets other than the pair of sheets sandwiching said second elastic members; and
said second elastic members are separated from said leg-surrounding elastic members by said third sheet lying between said second and leg-surrounding elastic members, thereby ensuring that said second elastic members are not secured to said leg-surrounding elastic members at the crossover points of said second and leg-surrounding elastic members.

3. The wearing article according to claim 1, further comprising a plurality of welding spots at which the sheets sandwiching said second elastic members are bonded together;
wherein said welding spots are formed in vicinities of transversely opposite side edges of said panel, lie between each pair of adjacent free middle portions of said second elastic members, and are spaced apart one from another by a predetermined distance in said longitudinal direction.

4. A pants-type disposable wearing article, comprising:
a liquid-impervious base sheet defining a front waist region, a rear waist region, and a crotch region extending between the front waist region and the rear waist region in a longitudinal direction of said article, said front and rear waist regions being attached to each other along transversely opposite side edges thereof so as to form a waist-hole and a pair of leg-holes;
a liquid-absorbent panel attached to an inner side of said base sheet;
a first elastic member extending along a peripheral edge of said waist-hole;
a plurality of second elastic members extending across said liquid-absorbent panel in at least one of said front and rear waist regions and between the transversely opposite side edges of said front and rear waist regions; and
a plurality of third elastic members extending along peripheral edges of said leg-holes;
wherein
each of said second elastic members has
opposite end portions located outward beyond transversely opposite side edges of said liquid-absorbent panel and being secured to said base sheet, and
a middle portion connecting said opposite end portions, extending between the transversely opposite side edges of said liquid-absorbent panel, and being free of direct attachment to both said base sheet and said liquid-absorbent panel; and
the middle portions of said second elastic members cross over said third elastic members and are not secured to said third elastic members at crossover points of said second and third elastic members; and
said base sheet comprises first and second sheets, said first sheet is disposed between said liquid-absorbent panel and said second sheet, and said second elastic members are disposed between said first and second sheets;
said base sheet further comprising bonding spots joining said first and second sheets in regions located between the middle portions of adjacent said second elastic members, said bonding spots limiting displacement of the middle portions of said second elastic members in the longitudinal direction of said article without affecting contraction of said middle portions in a transverse direction of said article.

5. The article of claim 4, wherein some of said bonding spots are arranged along said transversely opposite side edges of said panel and between entire said panel on the one hand and the end portions of said second elastic members on the other hand.

6. The article of claim 4, wherein said base sheet, in an entire region underlying said panel, is free of said bonding spots.

7. The article of claim 4, wherein said bonding spots are presented between every pair of adjacent said second elastic members so as to prevent said adjacent second elastic members from forming a bundle with each other.

8. The article of claim 2, wherein said third sheet carries printed indicia in a region corresponding to the middle portions of said second elastic members;
said third sheet being disposed between said second elastic member and said second sheet, and secured to said second sheet.

* * * * *